US010947282B2

(12) United States Patent
Bondos et al.

(10) Patent No.: US 10,947,282 B2
(45) Date of Patent: Mar. 16, 2021

(54) FUNCTIONALIZED PROTEIN-BASED MATERIALS AND THEIR USES

(71) Applicant: The Texas A&M University System, College Station, TX (US)

(72) Inventors: Sarah Bondos, College Station, TX (US); Kayla Bayless, Bryan, TX (US); Kathleen Matthews, Houston, TX (US); Jan Patterson, College Station, TX (US); Colette Abbey, College Station, TX (US); David Howell, College Station, TX (US); Hao-Ching Hsiao, San Diego, CA (US); Kelly Churion, College Station, TX (US); Shang-Pu Tsai, Brookline, ME (US); Sandhya Ramasamy, Katy, TX (US); Dustin Porterpan, Kingwood, TX (US); Keira Northern, Houston, TX (US)

(73) Assignees: The Texas A & M University System, College Station, TX (US); William Marsh Rice University, Houston, TX (US)

( * ) Notice: Subject to any disclaimer, the term of this patent is extended or adjusted under 35 U.S.C. 154(b) by 0 days.

(21) Appl. No.: 15/544,216

(22) PCT Filed: Jan. 20, 2016

(86) PCT No.: PCT/US2016/013977
§ 371 (c)(1),
(2) Date: Jul. 17, 2017

(87) PCT Pub. No.: WO2016/118538
PCT Pub. Date: Jul. 28, 2016

(65) Prior Publication Data
US 2018/0222949 A1    Aug. 9, 2018

Related U.S. Application Data

(60) Provisional application No. 62/105,132, filed on Jan. 19, 2015.

(51) Int. Cl.
| C07K 14/43 | (2006.01) |
| A61K 38/18 | (2006.01) |
| C07K 14/435 | (2006.01) |
| A61K 38/19 | (2006.01) |
| A61K 38/16 | (2006.01) |
| A61K 38/08 | (2019.01) |
| A61K 9/70 | (2006.01) |
| A61K 38/17 | (2006.01) |

(52) U.S. Cl.
CPC .......... *C07K 14/43581* (2013.01); *A61K 9/70* (2013.01); *A61K 9/7007* (2013.01); *A61K 38/08* (2013.01); *A61K 38/16* (2013.01); *A61K 38/1767* (2013.01); *A61K 38/1825* (2013.01); *A61K 38/1866* (2013.01); *A61K 38/195* (2013.01)

(58) Field of Classification Search
CPC ..................... C07K 14/43581; A61K 38/1825
See application file for complete search history.

(56) References Cited

U.S. PATENT DOCUMENTS

| 2003/0027751 A1 | 2/2003 | Kovesdi et al. |
| 2004/0029280 A1 | 2/2004 | Sosnowski et al. |
| 2010/0143436 A1* | 6/2010 | Bondos .............. C07K 14/4702 424/422 |
| 2013/0302400 A1 | 11/2013 | Maneval et al. |

OTHER PUBLICATIONS

Patterson et al., 2013 (published online Apr. 18, 2013), Materials composed of the *Drosophilia melanogaster* protein ultrabithorax are cytocompatible, J Biome Mater Res Part A, 102A: 97-104.*
Majithia et al., 2011, On the Design of Composite Protein-Quantum Dot Biomaterials via Self-Assembly, Biomacromolecules, 12: 3629-3637.*
Choo et al., 2014, Characterization of *Drosophilia* UbxCPTI000601 and hthCPTI000378 Protein Trap Lines, The Scientific World Journal, 2014: 14 pages.*
Alford et al., 2012, Dimerization-Dependent Green and Yellow Fluorescent Proteins, ACS Synth Biol, 1(12): 569-575.*
Charati et al., "Hydrophilic Elastomeric Biomaterials Based on Resilin-Like Polypeptides", Soft Matter, 2009, 11 pages.
Dinjaski et al., "Osteoinductive Recombinant Silk Fusion Proteins for Bone Regeneration", Acta Biomaterialia 49, 2017, 13 pages.
Hino et al., "The Generation of Germline Transgenic Silkworms for the Production of Biologically Active Recombinant Fusion Proteins of Fibroin and Human Basic Fibroblast Growth Factor", ScienceDirect, Biomaterials 27, 2006, 10 pages.
Pereira et al., "Silk-Based Biomaterials Functionalized With Fibronectin Type Ii Promotes Cell Adhesion", Acta Biomaterialia 47, 2017, 10 pages.
Zhou et al., "Self-Assembly of Amyloid Fibrils That Display Active Enzymes", ChemCatChem, 6, DOI: 10.1002/cctc.201402125, 2014, 9 pages.

(Continued)

*Primary Examiner* — Amber D Steele
(74) *Attorney, Agent, or Firm* — Winstead PC

(57) ABSTRACT

Embodiments of the invention are directed to Ubx-fusion molecules that maintain their mechanical strength and properties even after being fused with Ubx. Ubx fusions with VEGF and other growth factors, cell signaling proteins, and cell binding proteins can be used to induce angiogenesis. Ubx fibers and mesh, embedded within a tissue engineering scaffold, induce formation of vasculature within the scaffold. The presence of vasculature is necessary to provide oxygen and nutrients to other cells growing within the scaffold.

19 Claims, 2 Drawing Sheets

Specification includes a Sequence Listing.

(56) References Cited

OTHER PUBLICATIONS

Endrizzi et al, "Specific Covalent Immobilization of Proteins through Dityrosine Cross-Links", Langmuir 2006, vol. 22, pp. 11305-11310, published on Web Nov. 18, 2006.
Passner et al., "Structure of a DNA-bound Ultrabithorax-Extradenticle Homeodomain Complex", Nature, vol. 397, pp. 714-719, Feb. 25, 1999.
PIR_B27867, homeotic protein Ultrabithorax—fruit fly (*Drosophila melanogaster*) (fragment), NCBI Protein Accession No. B27867, Feb. 23, 1997 (online); retrieved from Internet: <URL:http://www.ncbi.nlm.nih.gov/protein/B27867?report=genpept>Definition, and Origin, retrieved on Mar. 24, 2016.
UniProtKB_Q964V4, Ubx protein, UniProtKB Accession No. Q964V4, Nov. 28, 2006 (online); retrieved from Internet: <URL:http://www.ncbi.nlm.nih.gov/protein/Q964V4>Definition, and Origin, the region between amino acid residues 13-73, retreived on Mar. 24, 2016.
Cross et al., "FGF and VEGF Function in Angiogenesis: Signalling Pathways, Biological Responses and Therapeutic Inhibition", Trends in Pharmacological Sciences, vol. 22 No. 4, pp. 201-207, Apr. 2001.

\* cited by examiner

FUNCTIONALIZED PROTEIN-BASED MATERIALS AND THEIR USES

CROSS-REFERENCES TO RELATED APPLICATIONS

This application claims the benefit under 35 U.S.C. § 119(e) of U.S. Provisional Patent Application No. 62/105,132, filed Jan. 19, 2015, which is incorporated herein by reference in its entirety as if fully set forth herein.

STATEMENT REGARDING FEDERALLY-SPONSORED RESEARCH OR DEVELOPMENT

This invention was made with government support under Grant No. R01HL095786 awarded by The National Institutes of Health and Grant No. R3E821 awarded by the National Science Foundation. The government has certain rights in the invention.

BACKGROUND

Proteins implement most of the vital molecular functions of living organisms, including providing structural support, generating energy, sensing biomolecules, and catalyzing, storing, and degrading important biomolecules. Proteins are particularly adept at highly specific molecular recognition, which can be adapted to bind virtually any ligand, ranging from small chemicals to specific types of cells. Such interactions are often regulated by the chemical environment, by binding additional ligands (allostery), or by post-translational modification of the protein.

Devices that capture proteins in materials have the potential to mimic these functions and be regulated by eternally applied factors. However, this approach is technically challenging. The three-dimensional structures of proteins are maintained by non-covalent bonds, which are sensitive to the surrounding medium. Perturbations of this chemical environment can easily result in loss of protein function. Proteins are commonly incorporated into materials either by physically trapping them within the matrix of the materials during assembly or by covalently crosslinking them to the surface of the materials post-assembly. Both of these approaches can result in the loss of functional proteins. Physically trapped proteins can be inactivated by the harsh chemical environment often used to instigate the assembly of the proteins into materials. Furthermore, the functional proteins are free to diffuse out of the materials. Although covalent crosslinking tethers functional proteins to the materials, the crosslinking agent can also inactivate the appended protein or remain embedded in the materials, rendering them toxic to cells. In addition, materials held together by non-covalent bonds may be too fragile for chemical modifications after assembly. Finally, depending on the specificity of the cross-linking strategy, some portion of the functional protein may be oriented such that the materials structure blocks ligand binding and hence protein function.

For materials composed of recombinant proteins, the use of protein fusions provides an attractive alternative. By fusing a gene encoding a functional protein to a gene encoding a self-assembling protein, a single polypeptide can be produced that contains the sequences of both proteins. This fusion protein should retain both the functional and self-assembly properties of the parent proteins. This method offers several advantages for incorporating functional proteins: (i) materials assembly and functionalization can be combined into a single step, (ii) stoichiometric levels of functionalization can be achieved, (iii) covalent attachment prevents loss of the functional protein due to diffusion, (iv) toxic byproducts (remnants of chemical cross-linking) are not created, and (v) the functional proteins can be patterned within the materials. In addition, all of the appended proteins have a uniform orientation, although there are only two possible points of attachment—the N- and C-termini of the self-assembling protein. The gene fusion approach requires mild conditions for materials assembly that will not perturb the structure of the appended functional protein.

Not every functional protein is a good candidate for incorporation into materials via gene fusion. Unstable or insoluble functional proteins could hamper expression of the fusion protein, or large/multimeric functional proteins may misposition the self-assembling protein, thus altering the mechanical properties of the materials or even preventing materials assembly. Thus, it is important for any functional protein to maintain its stability and properties.

The development of this invention was funded in part by the Welch Foundation under grant number C-0576.

SUMMARY

Embodiments of the invention are directed to Ubx-appended molecules that maintain their mechanical strength and properties even after being fused with Ubx. Ubx fusions with VEGF and other growth factors, cell signaling proteins, and cell binding proteins can be used to induce angiogenesis. Ubx fibers and mesh, embedded within a tissue engineering scaffold, induce formation of vasculature within the scaffold. The presence of vasculature is necessary to provide oxygen and nutrients to other cells growing within the scaffold.

DETAILED DESCRIPTION

Figure 1:
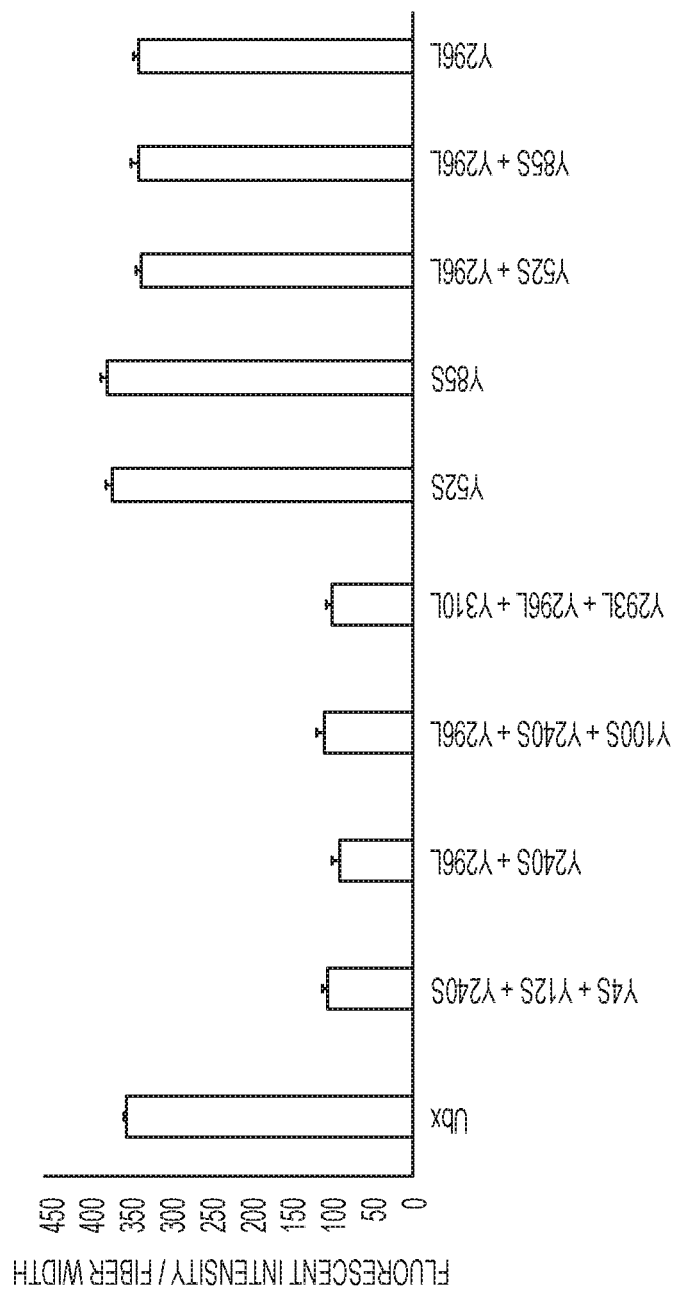
FIG. 1 shows a comparison of the fluorescence intensity of wild-type Ubx and several tyrosine mutants.

In an embodiment of the claimed invention, nanoscale to macroscale materials composed of the Drosophila melanogaster protein Ultrabithorax (Ubx) are generated. These materials are in the form of sheets, fibers, meshes, or fiber/mesh combinations. Ubx materials are biocompatible and non-immunogenic. The materials have mechanical properties appropriate for tissue engineering. The strength of Ubx materials derives from dityrosine covalent bonds that form spontaneously during assembly. Dityrosine bond content can be manipulated by mutagenesis to increase or decrease the strength of the materials. Chemical functions can be easily incorporated into Ubx materials in two ways. First, a gene encoding a protein with a useful function can be fused to the gene encoding Ubx. The resulting fusion gene, when transformed into E. coli, produces a fusion protein encompassing the sequences of both the functional protein and Ubx. Ubx fusion proteins retain the ability to assemble into materials. Furthermore, in the Ubx fusion proteins that have been tested thus far, the appended protein also retains its ability to function. Ubx fusions including the VEGF protein can induce angiogenic behaviors in endothelial cells. Cells can be layered on Ubx fibers (endothelial cells on a fiber, smooth muscle cells on top of the endothelial cells) to mimic the layers of cells in blood vessels. Additionally, fiber/mesh structures in which the morphology resembles that of a vascular bed can also be created. VEGF-Ubx fibers, when placed on top of a chicken embryo, induce the formation of vasculature.

The Ubx protein contains a DNA binding domain, and this domain remains folded and capable of binding DNA in a sequence-specific manner in Ubx materials. DNA sequences with multiple Ubx binding sites remain bound to Ubx materials for over a week, even though the Ubx-DNA interaction is non-covalent. A DNA bound to Ubx fibers will orient such that the region with the most Ubx binding sites is facing the fiber.

Ubx fusions with VEGF and other growth factors, cell signaling proteins, and cell binding proteins can be used to induce angiogenesis. Ubx fibers and mesh, embedded within a tissue engineering scaffold, should induce formation of vasculature within the scaffold. The presence of vasculature is necessary to provide oxygen and nutrients to other cells growing within the scaffold. Because all of the proteins that induce vasculature formation (angiogenic proteins) are only located on Ubx materials, they will not misinstruct cells in other locations in the scaffold (e.g., liver cells will not be instructed to become blood vessels). Because the angiogenic proteins are covalently bound to Ubx materials, they cannot diffuse away, thus losing the instructions or "fuzzing" the pattern.

Several proteins have been fused to Ubx to examine their impact on Ubx assembly and properties. Ubx self-assembles rapidly in gentle buffers to form films and fibers. Ubx materials are biocompatible, strong, and remarkably extensible. Furthermore, proteins fused to Ubx retain their activity once incorporated into materials. The proteins fused to Ubx were selected to test a range of sizes, structures, stabilities, solubility, and charges. It was found that the appended protein had a large effect on protein production, with the solubility and quaternary structure of the appended protein being the best predictors for success. In contrast, the ability to self-assemble into materials was dominated by Ubx, and the presence or identity of a fused protein had little impact on materials assembly. Although the appended protein can alter the mechanical properties of the materials, these properties, like those of Ubx fibers, (i) can be adjusted by varying fiber diameter and (ii) remain similar to the extracellular matrix protein elastin. In addition, unlike other self-assembling proteins found in nature, Ubx is unique in that it contains a DNA binding domain.

The presence of dityrosine provides an opportunity to manipulate the properties of Ubx materials by controlling dityrosine bond formation. Controlling dityrosine bond formation makes the Ubx protein easier to manipulate in the context of a fusion protein. Ubx has 15 tyrosine residues. The identity of tyrosines contributing to a single bond may vary, and more than one dityrosine bond may be present in the materials, creating an enormous array of possible bond arrangements. When bound to DNA, Ubx can oligomerize in multiple orientations: side-to-side cooperative interactions when binding to linear DNA, and back-to-back interactions between clusters of cooperatively bound Ubx proteins to form the stem of a DNA loop. Because Ubx fibers retain the ability to bind DNA, it is possible that interactions used on a small scale to enable cooperative DNA binding and DNA loop formation in vivo may also be applied on a much larger scale to form Ubx materials in vitro: side-to-side interactions to form nanoscale fibrils, and back-to-back interactions to allow the fibrils to interact to form films and fibers.

Two dityrosine bonds in Ubx are identified by site-directed mutagenesis followed by measurements of fiber fluorescence intensity. One bond is located between the N-terminus and the homeodomain (Y4/Y296, Y12/Y293), and another bond is formed by Y167 and Y240. The intensity of blue fluorescence corresponds with immunostaining using the antidityrosine primary antibody (confirming that changes in fiber fluorescence directly correspond to alterations in dityrosine content). FIG. 1 shows that the mutants Y4S+Y12S+Y240S, Y240S+Y296L, Y100S+Y240S+Y296L, and Y293L+Y296L+Y310L all show a loss of 250 fluorescence units per micrometer when compared to Ubx, suggesting a loss of more than one tyrosine bond However, mutation of tyrosines Y52 and Y85, which were not predicted to be involved in dityrosine bonds has no effect either in wild-type Ubx or in the Y296 background.

The Y167S and Y240S mutations both reduce fluorescence to a similar degree, suggesting that Y167 and Y240 participate in the same dityrosine bond. To test this hypothesis, a Y167S+Y240S double mutant was created. No further reduction in fluorescence was observed for the Y167S+Y240S double mutant (FIG. 1), suggesting that Y167 and Y240 form a single dityrosine bond. The Y167S+Y240S bond is responsible for a significant portion of the observed fluorescence in Ubx fibers (200/360 fluorescence units per micrometer).

Fiber fluorescence closely correlates with fiber strength, demonstrating that these bonds are intermolecular. The percentage of Ubx molecules harboring both bonds can be decreased or increased by mutagenesis, providing an additional mechanism to control the mechanical properties of Ubx materials. Duplication of tyrosine-containing motifs in Ubx increases dityrosine content in Ubx fibers, suggesting these motifs could be inserted in other self-assembling proteins to strengthen the corresponding materials.

Since adding an entire region of the Ubx protein might not be feasible for some self-assembling proteins, shorter sequences have been identified to replace the large insertion. The sequences surrounding tyrosines that form dityrosine bonds must contribute to interaction specificity, and thus would need to be transferred to the heterologous system. Based on Ubx sequence conservation, structure/disorder data, and the predicted propensity to engage in protein interactions, the below sequences are recommended for transfer to other proteins to create dityrosine bonds. For protein systems that can accommodate large insertions, the homeodomain (LRRRGRQTYTYQTLELEKE FHTNHYL-TRRRRIEMAHALCLTERQIKIWFQNRRMKLKKEI; SEQ ID NO: 1) and the N-terminus (MNSYFEQA; SEQ ID NO: 2) are used. As an additional benefit, the solubility and stability of the homeodomain is expected to improve protein production when fused to a self-assembling protein. For protein systems that can only tolerate small insertions or that self-assemble upon exposure to denaturing conditions, the conserved motifs surrounding residues 167 (VRPS-ACTPDSRVGGYLDTS; SEQ ID NO: 3) and 240 (FYPW-MAIA; SEQ ID NO: 4) are used. Thus the specific dityrosine-bond forming motifs in Ubx have the potential to be a useful tool for engineering the fluorescent and mechanical properties of other protein systems.

In certain embodiments of the claimed invention, the full length Ubx protein is used to create a fusion protein. In other embodiments of the invention, the Ubx protein that is used to form a Ubx fusion protein is a combination of SEQ ID NO: 1 and SEQ ID NO:2, or a combination of SEQ ID NO:3 and SEQ ID NO: 4.

In certain embodiments, Ubx fusion proteins are used to create materials that induce damaged endothelium in blood vessels to heal. Clogged arteries are typically re-opened by angioplasty, in which a balloon is inflated to open the artery, and a stent placed to hold the artery open. Both the initial damage and deployment of the stent damage the endothelial lining and can cause a clot to form, thus re-blocking the artery. Stents coated in functionalized Ubx materials have been shown to cause a new, healthy endothelial layer to form and prevent clot formation.

Because 3-dimensional structures can be easily designed and created using DNA, many materials are composed of DNA, or materials decorated with DNA with some engineered function. Since proteins can expand the possible functions or allow creation of more exotic shapes, there is interest in creating protein/DNA composite materials. Current approaches are to chemically crosslink protein to DNA (a method that is expensive, generates toxic byproducts, and possesses a geometry that is difficult to control), or to append a string of positively charged amino acids to the protein to get DNA to non-specifically bind (a method that has no control over geometry or orientation, and the binding is low affinity). On the other hand, Ubx materials bind DNA in a sequence specific manner, meaning there is control over affinity, patterning, and orientation. In certain embodiments, Ubx materials are coated in DNA sensors. Both the orientation of the DNA and the affinity of Ubx materials for DNA increases the sensitivity of these devices.

Ultrabithorax (Ubx) protein molecules have the ability to self-assemble. Ubx materials can be functionalized 1) more easily and cheaply 2) with defined orientations of the functional molecules and 3) with a greater range of functional molecules than other materials. This characteristic of Ubx proteins makes it possible to create protein composite materials that are not otherwise available.

It has previously been established that materials with Ubx fusion proteins can be made. However, the proteins used in those studies were small, stable, highly soluble, and monomeric and thus likely to succeed. Since that time, materials with large, less soluble, and/or multimeric proteins have been made, greatly expanding the range of proteins that can be used.

Figure 2:
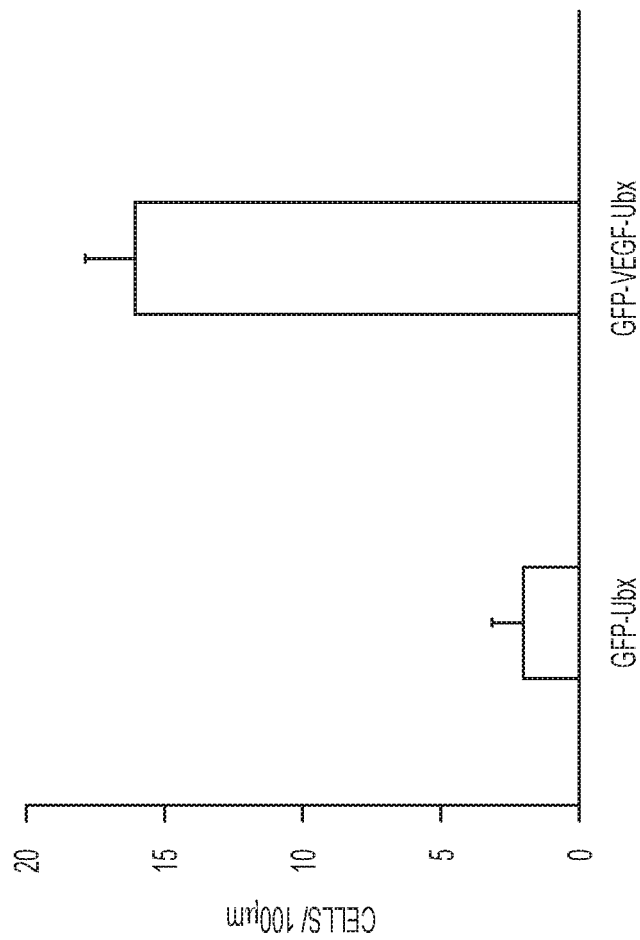
FIG. 2 shows that EGFP-VEGF-Ubx fibers promote enhanced recruitment and migration of endothelial cells.

In certain embodiments of the invention, a Ubx fusion protein with VEGF is created. This fusion is made with either the full length Ubx protein, a combination of SEQ ID NO: 1 and SEQ ID NO:2, or a combination of SEQ ID NO:3 and SEQ ID NO: 4. Studies with VEGF-Ubx (VEGF is a dimer) demonstrate that the fused protein is still active. VEGF-Ubx fibers induce formation of vasculature. Fusing the gene encoding vascular endothelial growth factor (VEGF) with the ultrabithorax (Ubx) gene, to produce fusion proteins capable of self-assembly into materials. VEGF-Ubx materials enhance human endothelial cell migration and prolong cell survival. FIG. 2 shows quantification of the number of cells/100 μm distance attached to EGFP-Ubx vs. EGFP-VEGF-Ubx fibers. A significantly greater number of cells migrated onto EGFP-VEGF-Ubx fibers when compared to control EGFP-Ubx fibers, indicating that VEGF-Ubx materials stimulated migration of ECs in low serum conditions. This approach provides an inexpensive and facile mechanism to stimulate and pattern angiogenesis.

Embodiments of the invention can be understood by reference to the following examples:

Creating Protein Fusions

The gene of the functional protein, followed by DNA encoding a flexible, water soluble linker, followed by the ubx gene, are placed in tandem without intervening stop codons. The linker DNA encodes alternating glycine and serine residues. Glycine provides flexibility and serine provides water solubility. This fusion gene is cloned into the pET-19b plasmid (it should be noted that other plasmids work equally well). The plasmid is transformed into *E. coli*. *E. coli* are fermented until the optical density reaches ~0.6-0.7, and then production of the fusion protein is induced with 1 mM IPTG. Depending on the solubility and stability of the fusion protein, the *E. coli* are allowed to produce the fusion protein between 2 and 16 hours.

Coating the Surface of Materials with DNA

Fibers are wrapped around a structural support and dipped into a buffer containing DNA. The DNA sequence needs to contain at least one Ubx binding sequence to adhere to Ubx materials.

Embedding DNA in the Materials

Ubx monomers are incubated with DNA prior to materials assembly. Both the Ubx and DNA concentrations need to be higher than 160 pM, the affinity constant.

Embedding Ubx Materials in Scaffolds

Ubx fibers are wrapped around a supporting structure (e.g. a plastic inoculation loop) or Ubx film is supported by the loop (think about soapy water in a bubble wand). The Ubx materials are then placed in a container, such as a well in a cell culture plate. The scaffold material (e.g., collagen) is then polymerized around the Ubx materials.

Creating Ubx Mesh

Ubx film is allowed to dry in air. We generally use inoculation loops to support the film, but other supports (e.g. plastic coated paper clips) work as well.

Creating Layers of Cells on Ubx Materials

Ubx fibers are dipped in the first cell type (endothelial cells) and the cells are allowed to attach. Subsequently, the fibers are moved to a culture containing the second cell type (smooth muscle cells) and these are given the opportunity to attach.

Creating Ubx Materials in Structures That Look Like Vascular Beds

Ubx fibers are wrapped around an inoculation loop or other support. The loop is used to pick up a Ubx film. When the film dries, the structure is complete.

While the invention has been particularly shown and described with references to example embodiments thereof, it will be understood by those skilled in the art that various changes in form and details may be made therein without departing from the scope of the invention encompassed by the appended claims.

What is claimed is:

1. A composition comprising at least one Ultrabithorax (Ubx) protein coupled with a first biomolecule, wherein the first biomolecule is a multimeric protein and is not Ubx, wherein the Ubx protein contains mutations within tyrosine residues involved in the formation of di-tyrosine bonds wherein the mutations within tyrosine residues influence formation of di-tyrosine bonds, alter the strength of Ubx materials, and/or alter intensity of blue fluorescence.

2. The composition of claim 1, further comprising a second biomolecule.

3. The composition of claim 2, wherein the second biomolecule is a highly soluble protein or an additional functional protein.

4. The composition of claim 1, wherein the Ubx protein contains mutations within tyrosine residues that are not involved in the formation of di-tyrosine bonds.

5. The composition of claim 1, wherein the dityrosine content is lower than in the wild type protein.

6. The composition of claim 1, wherein the dityrosine content is greater than in the wild type protein.

7. The composition of claim 1, wherein the first biomolecule is VEGF, FGF or SDF-1.

8. The composition of claim 1, wherein the composition is incorporated into a structure.

9. The composition of claim 8, wherein the structure is a mesh, film, fiber or a combination thereof.

10. The composition of claim 8, wherein the structure is coated with a protein.

11. The composition of claim 10, wherein the protein promotes angiogenesis.

12. The composition of claim 10, wherein the protein activates a signaling pathway.

13. The composition of claim 12, wherein the signaling pathway is the VEGF signaling pathway.

14. The composition of claim 8, wherein the structure is coupled with DNA.

15. The composition of claim 1, wherein the Ubx protein is selected from the group consisting of the full length Ubx protein, SEQ ID NO: 1, SEQ ID NO: 2, SEQ ID NO: 3 and SEQ ID NO: 4.

16. The composition of claim 1, wherein the Ubx protein is selected from the group consisting of the combination of SEQ ID NO: 1 and SEQ ID NO: 2 and the combination of SEQ ID NO: 3 and SEQ ID NO: 4.

17. A composition comprising at least one Ultrabithorax (Ubx) protein coupled with a first biomolecule, wherein the first biomolecule is a multimeric protein and is not Ubx, wherein the Ubx protein is selected from the group consisting of the full length Ubx protein, SEQ ID NO: 1, SEQ ID NO: 2, SEQ ID NO: 3 and SEQ ID NO: 4, and wherein the Ubx protein contains mutations within tyrosine residues involved in the formation of di-tyrosine bonds.

18. The composition of claim 17 wherein the mutations within tyrosine residues influence formation of di-tyrosine bonds, alter the strength of Ubx materials, or alter intensity of blue fluorescence.

19. A composition comprising at least one full-length ultrabithorx (Ubx) protein with substitutions within tyrosine residues involved in the formation of di-tyrosine bonds coupled with a first multimeric biomolecule which is not Ubx.

* * * * *

SEQUENCE LISTING

```
<160> NUMBER OF SEQ ID NOS: 4

<210> SEQ ID NO 1
<211> LENGTH: 60
<212> TYPE: PRT
<213> ORGANISM: Drosophila melanogaster
<220> FEATURE:
```

-continued

```
<221> NAME/KEY: SITE
<222> LOCATION: (1)..(60)
<220> FEATURE:
<221> NAME/KEY: SITE
<222> LOCATION: (1)..(60)
<223> OTHER INFORMATION: Dityrosine bond formation site

<400> SEQUENCE: 1

Leu Arg Arg Arg Gly Arg Gln Thr Tyr Thr Tyr Gln Thr Leu Glu Leu
1               5                   10                  15

Glu Lys Glu Phe His Thr Asn His Tyr Leu Thr Arg Arg Arg Arg Ile
            20                  25                  30

Glu Met Ala His Ala Leu Cys Leu Thr Glu Arg Gln Ile Lys Ile Trp
        35                  40                  45

Phe Gln Asn Arg Arg Met Lys Leu Lys Lys Glu Ile
    50                  55                  60

<210> SEQ ID NO 2
<211> LENGTH: 8
<212> TYPE: PRT
<213> ORGANISM: Drosophila melanogaster
<220> FEATURE:
<221> NAME/KEY: SITE
<222> LOCATION: (1)..(8)
<220> FEATURE:
<221> NAME/KEY: SITE
<222> LOCATION: (1)..(8)
<223> OTHER INFORMATION: Dityrosine bond formation site

<400> SEQUENCE: 2

Met Asn Ser Tyr Phe Glu Gln Ala
1               5

<210> SEQ ID NO 3
<211> LENGTH: 19
<212> TYPE: PRT
<213> ORGANISM: Drosophila melanogaster
<220> FEATURE:
<221> NAME/KEY: SITE
<222> LOCATION: (1)..(19)
<220> FEATURE:
<221> NAME/KEY: SITE
<222> LOCATION: (1)..(19)
<223> OTHER INFORMATION: Dityrosine bond formation site

<400> SEQUENCE: 3

Val Arg Pro Ser Ala Cys Thr Pro Asp Ser Arg Val Gly Gly Tyr Leu
1               5                   10                  15

Asp Thr Ser

<210> SEQ ID NO 4
<211> LENGTH: 8
<212> TYPE: PRT
<213> ORGANISM: Drosophila melanogaster
<220> FEATURE:
<221> NAME/KEY: SITE
<222> LOCATION: (1)..(8)
<220> FEATURE:
<221> NAME/KEY: SITE
<222> LOCATION: (1)..(8)
<223> OTHER INFORMATION: Dityrosine bond formation site

<400> SEQUENCE: 4

Phe Tyr Pro Trp Met Ala Ile Ala
1               5
```